United States Patent
Ishikawa (10) Patent No.: US 8,888,977 B2
(45) Date of Patent: Nov. 18, 2014

(54) COMBINATION ELECTRODE FOR ION CONCENTRATION MEASUREMENT

(75) Inventor: Yoichi Ishikawa, Shinjuku-ku (JP)

(73) Assignee: Able Corporation, Tokyo (JP)

( * ) Notice: Subject to any disclaimer, the term of this patent is extended or adjusted under 35 U.S.C. 154(b) by 0 days.

(21) Appl. No.: 13/581,770

(22) PCT Filed: Feb. 17, 2011

(86) PCT No.: PCT/JP2011/053328
§ 371 (c)(1),
(2), (4) Date: Aug. 29, 2012

(87) PCT Pub. No.: WO2011/108361
PCT Pub. Date: Sep. 9, 2011

(65) Prior Publication Data
US 2012/0325660 A1 Dec. 27, 2012

(30) Foreign Application Priority Data
Mar. 1, 2010 (JP) .................................. 2010-061476

(51) Int. Cl.
*G01N 27/36* (2006.01)
*G01N 27/403* (2006.01)

(52) U.S. Cl.
CPC .................................. *G01N 27/4035* (2013.01)
USPC ......................................... 204/420; 204/416

(58) Field of Classification Search
CPC ..... G01N 27/30; G01N 27/36; G01N 27/403; G01N 27/4035; G01N 27/401; G01N 33/5438; Y10S 65/06
USPC .................. 204/280, 408, 416–420; 205/789, 205/787.5, 789.5; 422/82.03; 324/438; 65/DIG. 6
See application file for complete search history.

(56) References Cited

U.S. PATENT DOCUMENTS

| 4,012,308 A * | 3/1977 | Jerrold-Jones et al. ....... 204/420 |
| 4,608,148 A * | 8/1986 | Frollini et al. ................ 204/408 |
| 2010/0126850 A1* | 5/2010 | Franzheld et al. ............ 204/283 |

FOREIGN PATENT DOCUMENTS

| JP | 60-152956 U | 10/1985 |
| JP | 1-156454 U | 10/1989 |
| JP | 8-145937 A | 6/1996 |
| JP | 8-285811 A | 11/1996 |

OTHER PUBLICATIONS

Ito Satoshi, "pH No Sokutei to pHKei No Kanri (pH measurement and management of pH meter)", Kougyou Yousui (Industrial Water), Japan, Japan Industrial Water Association, Jul. 1986, pp. 49-59, vol. 334.

* cited by examiner

*Primary Examiner* — J. Christopher Ball
(74) *Attorney, Agent, or Firm* — Sughrue Mion, PLLC (57) ABSTRACT

A combination electrode for ion concentration measurement is provided including a glass electrode and a reference electrode whose internal electrode is made of silver-silver chloride, wherein a sealing means is provided configured to seal an upper surface of a reference electrode chamber formed in an outer tube which houses an internal electrode and an internal solution of the reference electrode, and around a glass support tube penetrating the outer tube along a substantially center axis thereof an annular silver member which the glass support tube penetrates along a center axis thereof, annular sealing elastic members for liquid-tightly sealing a space between the silver member and the glass support tube, and a space between the silver member and the outer tube, respectively, and the reference electrode internal electrode is connected to a terminal for a reference electrode through the silver member.

4 Claims, 4 Drawing Sheets

Figure 4

COMBINATION ELECTRODE FOR ION CONCENTRATION MEASUREMENT

CROSS REFERENCE TO RELATED APPLICATIONS

This application is a National Stage of International Application No. PCT/JP2011/053328 filed Feb. 17, 2011, claiming priority based on Japanese Patent Application No. 2010-061476 filed Mar. 1, 2010, the contents of all of which are incorporated herein by reference in their entirety.

TECHNICAL FIELD

The present invention relates to a combination electrode for ion concentration measurement, and more specifically to a combination electrode which includes a glass electrode and a reference electrode, and which is used for measuring the concentrations of ions such as hydrogen ions, sodium ions, or other monovalent cations.

BACKGROUND ART

When microorganisms, cells or tissues of animals or plants, or the like are cultured, it is extremely important for culture control to measure the concentrations of hydrogen ions, sodium ions, other monovalent cations, and the like in culture liquids. In general, combination electrodes for ion concentration measurement (hereinafter, simply referred to as "combination electrodes" in some cases) are used for this measurement.

Figure 4:
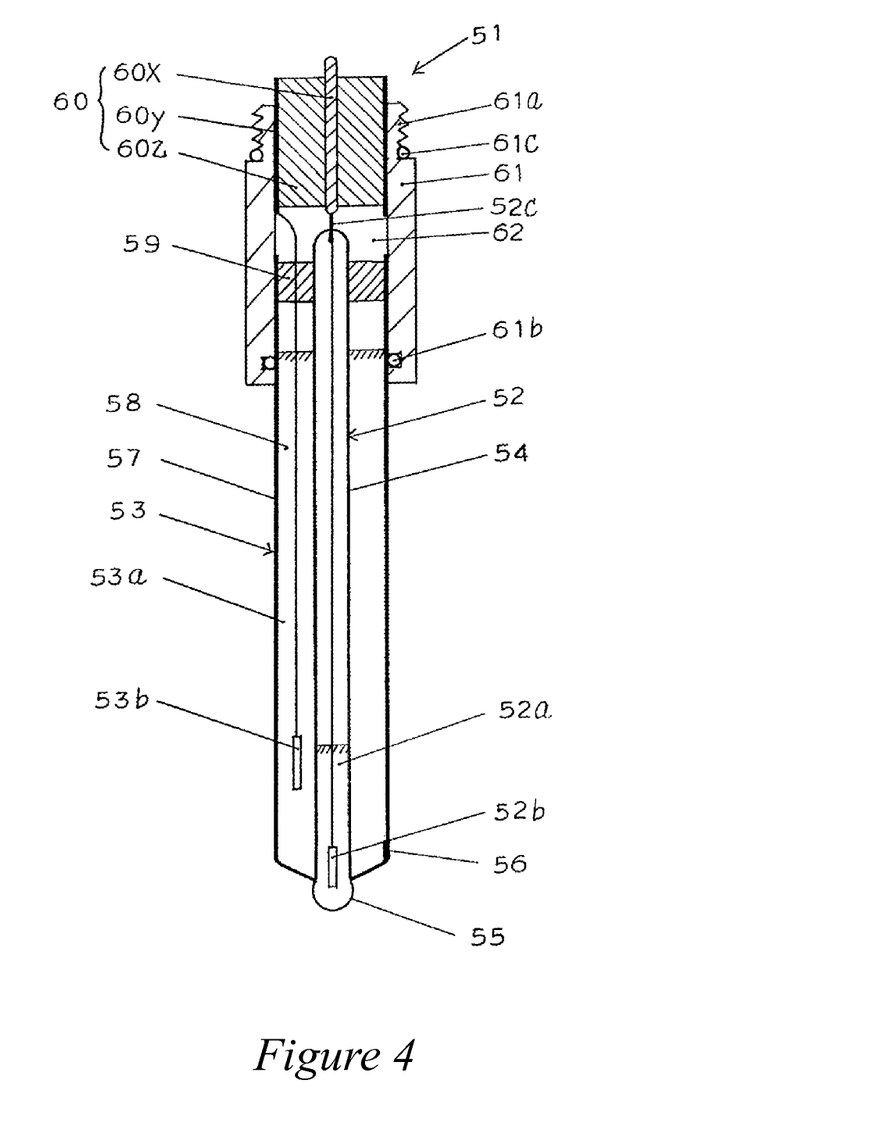
FIG. 4 is a schematic cross-sectional view of a combination electrode for ion concentration measurement of a conventional example.

A combination electrode for hydrogen ion concentration measurement, which is a so-called pH combination electrode, is known as a typical example of the combination electrodes for ion concentration measurement. FIG. 4 schematically shows an example of the structure of the combination electrode.

In the figure, the combination electrode 51 for ion concentration measurement includes a glass electrode (ion-selective electrode) 52 and a reference electrode 53.

The glass electrode 52 has a glass support tube 54 whose upper end is sealed, and which has a sensitive glass membrane 55 at a lower end thereof.

Here, an electric potential generated on a surface of the sensitive glass membrane 55 is generally taken out of the glass support tube 54 by a glass electrode internal solution 52a (a phthalate buffer solution or the like) housed on an backside (inside) of the sensitive glass membrane 55, and by: a silver wire of silver-silver chloride serving as a glass electrode internal electrode 52b; or a platinum wire 52c which is connected to an end portion of the silver wire in the glass support tube 54, and which penetrates an upper end-sealing portion. Then, the electric potential is transmitted to a lead wire (not illustrated) to a potentiometer through a terminal 60x for a glass electrode of a terminal portion 60, which will be described later.

Note that the silver wire of the internal electrode 52b may be employed for the portion penetrating the upper end-sealing portion of the glass supporting tube 54. Alternatively, a platinum wire, which has a thermal expansion coefficient close to that of glass, is often employed for the portion in a way that the platinum wire is sealed with glass.

The reference electrode 53 includes a closed reference electrode chamber 58 whose upper and lower surfaces are sealed, and which houses a reference electrode internal electrode 53b made of silver-silver chloride and a reference electrode internal solution 53a (a potassium chloride solution or the like). The reference electrode chamber 58 is formed inside an outer tube 57 and around the glass support tube 54. The outer tube 57 is made of glass or a synthetic resin, and has a liquid junction 56 near a lower end thereof. The glass support tube 54 is placed penetrating the outer tube 57 along a substantially center axis of the outer tube 57.

Note that the reference electrode internal solution 53a contains 1 to 5% (W/V) of a thickener (for example, carboxymethyl cellulose (CMC) or the like) in some cases, to prevent excessive seepage of the reference electrode internal solution 53a through the liquid junction 56 due to thermal expansion of the reference electrode internal solution 53a during a sterilization treatment of the combination electrode 51, which will be described later.

For the sealing of the upper surface (annular) of the reference electrode chamber 58, a filler of a synthetic resin (for example, a silicone resin or the like) being filled in an annular shape for sealing is used generally as a sealing means 59. Meanwhile, the sealing of the lower surface of the reference electrode chamber 58 is achieved, for example, by being melted and integrally welded to a portion near a lower end of the glass support tube 54, as shown in the figure, or by using a gasket.

Here, an electric potential of the reference electrode internal electrode 53b is taken out of the reference electrode chamber 58 by a silver wire of the reference electrode internal electrode 53b penetrating the sealing means 59 in the vertical direction. Then, the electric potential is transmitted to a lead wire (not illustrated) to a potentiometer through a terminal 60y for a reference electrode of the terminal portion 60, which will be described next.

The terminal portion 60 provided above the glass electrode 52 and the reference electrode 53 is configured such that the rod-shaped terminal 60x for a glass electrode is installed upright, while penetrating a sealing member 60z (for example, a filler of a synthetic resin (Example: polytetrafluoroethylene) or the like) along a substantially center axis thereof. The sealing member 60z sections the inside of the cylindrical terminal 60y for a reference electrode in the vertical direction.

In addition, the terminal portion 60 is connected to the glass electrode 52 and the reference electrode 53 by inserting and fixing the terminal portion 60 and an upper portion of the outer tube 57 into and to a cylindrical connecting member 61 in the vertical direction.

Note that an outer periphery of the terminal 60y and an inner periphery of the connecting member 61 are liquid-tightly fixed to each other by an adhesive agent made of a synthetic resin.

In addition, the impedance of the sensitive glass membrane 55 is generally as high as around 100 MΩ. Hence, an insulating property far greater than the impedance is required between the terminal 60x and the terminal 60y. Accordingly, the sealing member 60z needs to have an insulating property, and to avoid deterioration in insulation due to attachment of water or the like.

In a portion (a space portion and the like) 62 formed by being surrounded by a lower surface of the sealing member 60z of the terminal portion 60, an upper surface of the sealing means 59 of the reference electrode chamber 58, the glass support tube 54 and the like, and an inner peripheral surface of the connecting member 61, an end portion of the platinum wire 52c (or a silver wire, hereinafter the same shall apply) led to the outside of the glass support tube 54 and an end portion of the silver wire led from the reference electrode internal electrode 53b to the outside of the reference electrode chamber 58 are connected to lower ends of the terminal 60x and the terminal 60y, respectively. Here, the space portion and the like 62 is left as a space portion, as it is, or is filled with a filler of a synthetic resin (for example, a silicone resin or the like), for example.

In addition, a male screw 61a is provided on an upper outer periphery of the connecting member 61. A connector (not illustrated) to be connected to a potentiometer through a lead wire is screwed to the male screw 61a. Thereby, electric potentials of the glass electrode 52 and the reference electrode 53 are transmitted to the potentiometer.

Note that reference sign 61b denotes an O-ring interposed between the inner peripheral surface of the connecting member 61 and an outer peripheral surface of the outer tube 57, and reference sign 61c denotes an O-ring for liquid-tightly mounting a sterilization cap, which will be described later (see Non Patent Literature 1).

CITATION LIST

Non Patent Literature

[Non Patent Literature 1] Ito Satoshi, "pH No Sokutei To pHKei No Kanri (pH measurement and management of pH meter)," Kougyou Yousui (Industrial Water), Japan, Japan Industrial Water Association, July 1986, Vo. 334, p. 49 to 59

SUMMARY OF INVENTION

Technical Problems

When a combination electrode for ion concentration measurement as described above is used for culturing microorganisms, cells or tissue of an animal or plant, or the like, the combination electrode has to be subjected to a sterilization treatment.

Examples of the sterilization treatment include a case where an entire apparatus with the combination electrode kept attached is sterilized in an autoclave, as in the case of a mini-jar fermenter or the like; a case of a so-called built-in steam sterilization where the inside of a tank to which the combination electrode is attached is sterilized with steam (the combination electrode is subjected to the sterilization treatment only at a portion to be in contact with a culture liquid), as in the case of a built-in culture tank or the like; and the like. The sterilization conditions in these cases are, for example, 121° C. (0.1 MPa), 30 minutes, and so on.

However, when the combination electrode 51 as described above is subjected to the sterilization treatment under such conditions, the reference electrode internal solution 53a enters the space portion and the like 62 above the reference electrode chamber 58 for the following reason. Particularly because the coefficient of thermal expansion of the annular sealing means 59 made of a filler of a synthetic resin is different from the coefficients of thermal expansion of the glass support tube 54 on the inner periphery thereof, the outer tube 57 on the outer periphery thereof, and further the silver wire of the reference electrode internal electrode 53b which penetrates the sealing means 59 in the vertical direction, the filler is, for example, peeled off from contact surfaces therewith due to thermal cycles of the sterilization treatment, so that gaps are formed. As a result, the liquid tightness of the contact surfaces is impaired, and the impaired liquid tightness leads to the entering of the reference electrode internal solution 53a into the space portion and the like 62.

Accordingly, since the platinum wire 52c from the glass electrode internal electrode 52b is located in the space portion and the like 62 as described above, insulation failure occurs between the glass electrode internal electrode 52b and the reference electrode internal electrode 53b because of the reference electrode internal solution 53a which enters the space portion and the like 62.

Specifically, when the space portion and the like 62 is left as a space, as it is, insulation failure occurs between the platinum wire 52c from the glass electrode internal electrode 52b and the silver wire from the reference electrode internal electrode 53b because of the reference electrode internal solution 53a which enters the space portion and the like 62.

Moreover, even when the space portion and the like 62 is filled with a filler of a synthetic resin, the liquid tightness of the contact surfaces of the filler with the glass support tube 54 and with the platinum wire 52c from the glass electrode internal electrode 52b is impaired due to thermal cycles of the sterilization treatment, as in the above-described case. Eventually, insulation failure occurs between the two internal electrodes 52b, 53b, as in the above-described case, because of the reference electrode internal solution 53a which enters the space portion and the like 62.

For this reason, there arise problems of no generation of an electric potential difference between the glass electrode 52 and the reference electrode 53, an unstable output, and the like, which make the ion concentration measurement impossible, and the measurement values unstable, for example.

Note that the coefficients of thermal expansion are different on contact surfaces of the sealing member 60z made of the filler of the synthetic resin in the terminal portion 60 with the terminal 60x penetrating the sealing member 60z and with the terminal 60y, and further on a contact surface of the terminal 60y with the adhesive agent on the outer periphery thereof, as in the above-described case. Hence, the liquid tightness is also impaired on these contact surfaces due to the thermal cycles of the sterilization treatment.

However, in the case of the autoclave sterilization where the entire combination electrode 51 is subjected to the sterilization treatment, the sterilization cap (not illustrated) is liquid-tightly screwed onto the male screw 61a in the upper portion of the connecting member 61 with the O-ring 61c interposed in between before the sterilization. Thereby, the entering of steam from a portion above the combination electrode 51 is prevented during the sterilization treatment. Meanwhile, in the case of the built-in steam sterilization, the upper portion of the combination electrode 51 near the terminal portion 60 is not subjected to the sterilization treatment. Hence, no entering of steam from the portion above the combination electrode 51 occurs. Accordingly, the problems as described above do not arise in either case.

The present invention has been made in view of such problems with the conventional technology, and an object thereof is to prevent the problem of a combination electrode for ion concentration measurement including a glass electrode and a reference electrode due to thermal cycles of the conventional sterilization treatment, i.e., the leakage and entering of a reference electrode internal solution into a portion above a sealing means of a reference electrode chamber, and thereby to provide a combination electrode capable of stably measuring ion concentration with the insulation between a glass electrode internal electrode and a reference electrode internal electrode being secured.

Solution to Problems

To achieve this object, the present inventor first conceived that an upper end of an outer tube to form an upper portion of a reference electrode chamber should be melted while a platinum wire connected to an end portion of a silver wire penetrated the upper end of the outer tube as in the case with the upper end of the glass electrode. However, it was found that sealing by melting was difficult in this method in the case of a closed-type reference electrode having no supply port for a reference electrode internal solution, because the outer tube had a large diameter, and consequently had a large heat capacity, so that the reference electrode internal solution evaporated or boiled due to the heating during the melting, in contrast to the case of the glass electrode internal solution. It was also found that, particularly when the entire length of the outer tube was short, the sealing was further difficult, because the distance between the upper surface of the reference electrode internal solution and the sealing portion was inevitably short.

Then, the present inventor has made further investigation. As a result, the following new findings and the like have been obtained. Specifically, even slight deformation due to heat makes it impossible for the sealing means for the upper surface (annular) of the reference electrode chamber with a filler of a synthetic resin as in the conventional case to keep the liquid tightness (closure), because the filler is not elastic. In order to take out the electric potential of a reference electrode internal electrode to a portion above a reference electrode chamber without penetration through the sealing means made of the filler, an annular silver member made of the same material as that of a silver wire of silver-silver chloride, which serves as a reference electrode internal electrode, is used as one sealing means; and annular sealing elastic members for liquid-tightly sealing a space between the inner periphery of the silver member and the outer periphery of a glass support tube which penetrates the silver member along a substantially center axis thereof, and a space between the silver member and the outer tube, respectively, are used as other sealing means. In such a case, the leakage and entering of the reference electrode internal solution to a portion above the reference electrode chamber is prevented, so that insulation is secured between a glass electrode internal electrode and a reference electrode internal electrode. As a result, ion concentration can be measured stably. Based on the findings, the present invention has been completed.

Specifically, a combination electrode for ion concentration measurement of the present invention is a combination electrode for ion concentration measurement which includes a glass electrode and a reference electrode, characterized in that: the glass electrode includes a glass support tube and a sensitive glass membrane at a lower end of the glass support tube; the reference electrode includes a closed reference electrode chamber whose upper and lower surfaces are sealed, a reference electrode internal electrode made of silver-silver chloride, and a reference electrode internal solution, the reference electrode chamber being formed inside an outer tube having a liquid junction near a lower end thereof and around the support tube placed penetrating the outer tube along a substantially center axis thereof, the reference electrode internal electrode and the reference electrode internal solution being housed in the reference electrode chamber; a sealing means configured to seal the upper surface of the reference electrode chamber includes an annular silver member which the glass support tube penetrates along a substantially center axis thereof, and annular sealing elastic members for liquid-tightly sealing a space between an inner periphery of the silver member and an outer periphery of the glass support tube, and a space between the silver member and the outer tube, respectively; and the reference electrode internal electrode is connected to a terminal for a reference electrode through the silver member.

A preferable mode of the combination electrode for ion concentration measurement of the present invention is characterized in that the annular silver member has any one of a disk shape and a cylindrical shape.

Another preferable mode of the combination electrode for ion concentration measurement of the present invention is characterized in that the annular sealing elastic members are made of rubber.

Advantageous Effects of Invention

In the present invention, in order to take out the electric potential of the reference electrode internal electrode to the portion above the reference electrode chamber, the annular silver member made of the same material as the silver wire of silver-silver chloride which is the reference electrode internal electrode, and the annular sealing elastic members for liquid-tightly sealing the space between the inner periphery of the silver member and the outer periphery of the glass support tube, as well as the space between the silver member and the outer tube by being placed in the spaces, respectively, are used as the sealing means for the upper surface of the reference electrode chamber. Accordingly, the problem due to the thermal cycles of the conventional sterilization treatment, i.e., the leakage and entering of the reference electrode internal solution into the portion above the reference electrode chamber is prevented, so that the insulation is secured between the glass electrode internal electrode and the reference electrode internal electrode. As a result, the present invention makes it possible to provide a combination electrode for ion concentration measurement capable of stably measuring ion concentration.

DESCRIPTION OF EMBODIMENTS

First, a combination electrode for ion concentration measurement of the present invention includes a glass electrode and a reference electrode.

The glass electrode has a glass support tube whose upper end is sealed, and which has a sensitive glass membrane at a lower end thereof. The glass electrode is an ion-selective electrode having the glass membrane as a sensing portion. An electric potential generated on a surface of the sensitive glass membrane is taken out of the upper end of the glass support tube by, for example, a glass electrode internal solution, and, as described above, a silver wire of silver-silver chloride which is the glass electrode internal electrode, or a platinum wire which is connected to an end portion of the silver wire in the glass support tube, and which penetrates an upper end-sealing portion. Then, the electric potential is transmitted to a potentiometer through a terminal for a glass electrode.

Note that, as is publicly known, the sensitive glass membrane is used as a membrane responsive to hydrogen ions, sodium ions, other monovalent cations, or the like, by changing the composition thereof.

The reference electrode has a closed reference electrode chamber whose upper and lower surfaces are sealed, and which houses a reference electrode internal electrode made of silver-silver chloride and a reference electrode internal solution (potassium chloride or the like). The reference electrode chamber is formed inside an outer tube having a liquid junction near a lower end thereof, and around the support tube placed penetrating the outer tube along a substantially center axis thereof.

In addition, the lower surface of the reference electrode chamber is sealed, for example, by being melted and integrally welded to a lower end of the glass support tube, or by use of an appropriate gasket or the like.

Note that the material of the outer tube may be any of glass and a synthetic resin (Example: polyphenylene sulfide (PPS)).

In addition, as is publicly known, various structures are employed for the reference electrode internal electrode made of silver-silver chloride, and examples thereof include a silver wire plated with silver chloride, a silver wire to which molten silver chloride is welded, and the like.

The most noticeable feature of the combination electrode for ion concentration measurement of the present invention is the use of an annular silver member made of the same material as that of the silver wire of the reference electrode internal electrode, and annular sealing elastic members for liquid-tightly sealing a space between an inner periphery of the silver member and an outer periphery of the glass support tube as well as a space between the silver member and the outer tube, as a sealing means configured to seal the upper surface of the reference electrode chamber.

Thus, an electric potential of the reference electrode internal electrode is taken out from the silver member, specifically, from an upper surface or an upper end of the silver member to whose lower surface (lower end) an end portion of the silver wire of the internal electrode is connected by welding or the like, if necessary through a conductive member. Further, the electric potential is transmitted to a potentiometer through a terminal for a reference electrode.

Note that, in addition to the above-described reference electrode internal electrodes made of silver-silver chloride, a reference electrode internal electrode is also known in which a platinum wire plated with silver is inserted into a silver chloride powder layer housed in a container which allows the reference electrode internal solution to flow therethrough (a modified type in which the electric potential is taken out of the reference electrode chamber through the platinum wire). Here, platinum can be treated in the similar manner to that of silver, and regarded as silver, because platinum does not influence the electric potential even when it is in contact with the reference electrode internal solution.

The position at which the upper surface of the reference electrode chamber of the reference electrode is sealed may be, for example, an upper end of the outer tube (an outer tube extension extended upwardly from an upper portion of the outer tube is also included in the "outer tube" of the present invention), a position in the outer tube and near the upper end thereof, or the like. Horizontal sealing at a position of the upper end of the outer tube is preferable, because this sealing is easier.

Note that, since the inside of the outer tube is generally narrow, it tends to be difficult to form a sealing structure therein. However, the sealing conducted at the upper end of the outer tube is easier, because a space above the upper end of the outer tube can be used effectively.

The silver member is annular, because the glass support tube penetrates the silver member along a substantially center axis thereof. Examples of the shape of the silver member include a disk shape, a cylindrical shape, and the like.

In the case of a disk-shaped silver member, an inner diameter of the silver member is preferably slightly larger than an outer diameter of the glass support tube. Meanwhile, an outer diameter of the silver member is preferably substantially equal to an outer diameter of the outer tube, when the sealing position is the upper end of the outer tube. The outer diameter thereof is preferably substantially equal to the inner diameter of the outer tube, when the sealing position is the inside of the outer tube.

The thickness of the silver member is preferably 1 to 4 mm, for example.

Here, the silver member has both a sealing function and an electric potential-transmitting function.

Meanwhile, in the case of a cylinder-shaped silver member, the silver member is used with annular sealing elastic members, which will be described next, being placed outside and inside of the cylinder (Example: thickness: 0.5 to 1 mm, height: 2 to 4 mm), respectively. Here, the silver member has mainly an electric potential-transmitting function.

No specific restriction is imposed on each of the annular sealing elastic members, as long as the annular sealing elastic member is a member for sealing which is annular and has elasticity. For example, a rubber such as a synthetic rubber (Examples: a nitrile rubber, a styrol rubber, a silicone rubber, a fluorine rubber, an ethylene-propylene-diene rubber (EPDM), or the like)), a natural rubber or the like is preferably used.

In addition, it is a matter of course that an elastic member having excellent heat resistance is particularly preferable, because the combination electrode is subjected to the sterilization treatment as described above.

No specific restriction is imposed on a cross-sectional shape of the annular elastic member. Examples thereof include an O-ring, a D-ring, an X-ring and the like, and an O-ring is particularly preferable.

In addition, the annular elastic members liquid-tightly seal a space between the silver member and the glass support tube, and a space between the silver member and the outer tube, when the annular elastic members are mounted on their mounting portions, and distorted by application of an appropriate external force (by compression) by an external-force application member.

No specific restriction is imposed on a method for sealing the upper surface of the reference electrode chamber by use of the sealing means which includes a combination of the silver member and the elastic members, and specific examples thereof include the following methods.

(1) A case where the upper end of the outer tube is sealed:

In this case, an auxiliary tube into whose lower portion the upper portion of the outer tube is fitted is used, and the upper end of the outer tube in the auxiliary tube is sealed.

In this method, an annular silver member (having a disk shape with an inner diameter slightly larger than the outer diameter of the glass support tube, and an outer diameter substantially equal to the outer diameter of the outer tube) which the glass support tube penetrates along a substantially center axis thereof is placed on an upper end surface of the outer tube, with an annular elastic member (an outer elastic member: an O-ring or the like) interposed in between. In addition, another annular elastic member (an inner elastic member: an O-ring or the like) is placed on an upper surface of the silver member and near an inner circumferential edge thereof, with the glass support tube being inserted through the elastic member. Then, the upper end of the outer tube is sealed by pressing and compressing the latter and inner elastic member from above by use of an appropriate external-force application member (see Example 1).

Note that, the silver wire of the reference electrode internal electrode, or in the case of the above-described modified reference electrode, a platinum wire, is connected in advance to a lower surface of the silver member by welding or the like. If necessary, the silver wire or the platinum wire has an expandable and contractible spiral shape or the like.

In addition, the auxiliary tube can also serve as a connecting member for connecting a terminal portion, which will be described later, and the upper portion of the outer tube to each other.

As a result, both the outer and inner elastic members are distorted simultaneously, so that the space between the silver member (the lower surface thereof near an outer circumferential edge thereof) and the outer tube (the upper end surface thereof), and the space between the inner periphery of the silver member and the outer periphery of the glass support tube are liquid-tightly sealed.

Note that as a mounting portion of the outer elastic member, a recess may be provided at the outer circumferential edge of the lower surface of the silver member, or a space may be provided by the auxiliary tube and a taper which is formed on the upper end surface of the outer tube, and whose diameter becomes gradually smaller towards its upper end, for example.

Meanwhile, as a mounting portion of the inner elastic member, a recess may be provided at an inner circumferential edge of the upper surface of the silver member, or a space may be provided by the upper surface of the silver member and a taper in which is formed at an lower end of the external-force application member, and whose diameter becomes gradually larger towards its lower end, for example.

(2) A case where a portion in the outer tube and near the upper end thereof is sealed:

In this method, a sealing means is used in which an annular elastic member (inner elastic member) is fitted into an inner periphery of an annular silver member (having a cylindrical shape), and another annular elastic member (outer elastic member) is fitted onto an outer periphery of the annular silver member. Here, the inner elastic member whose inner diameter is smaller than an outer diameter of the glass support tube is used, and the outer elastic member whose outer diameter is larger than an inner diameter of the outer tube is used. The sealing means is inserted, mounted, and sealed in the outer tube by pressing the upper surface of the sealing means by use of an appropriate external-force application member, while the glass support tube is inserted through the inner elastic member (see Example 2).

Note that, as in the case of the above-described (1), the silver wire (or the platinum wire) of the reference electrode internal electrode is connected in advance to the lower end of the silver member by welding or the like. If necessary, the silver wire (or the platinum wire) has an expandable and contractible spiral shape or the like.

For inserting the sealing means into the outer tube in this case, a method is employed in which the sealing means is pressed and gradually inserted into the outer tube through an upper end opening of the outer tube in advance shaped like a funnel whose diameter becomes gradually larger toward an upper end thereof, by use of an external-force application member capable of uniformly pressing the upper surface of the sealing means, for example.

As a result, both the outer and inner elastic members are distorted simultaneously, so that the space between the silver member (the outer periphery) and the outer tube (the inner periphery), and the space between the inner periphery of the silver member and the outer periphery of the glass support tube are liquid-tightly sealed.

Note that this sealing method is effective when the inner diameter of the outer tube is large (for example, 8 mm or larger).

An electric potential of the reference electrode is, as described above, connected to a terminal for a reference electrode from the upper surface or the upper end of the silver member of the sealing means, through or not through a conductive member (which is formed in an expandable and contractible spiral shape or the like, if necessary).

In addition, the terminal portion including the terminal for a glass electrode, the terminal for a reference electrode, and the like is connected to the glass electrode and the reference electrode such that the terminal portion and the upper portion of the outer tube are inserted into and liquid-tightly fixed in the cylindrical connecting member with an O-ring or the like being used, in the vertical direction.

As a result, the insulation is secured at a connecting portion (a space below the terminal portion and above the sealing means) in the connecting member, and, of course, the insulation between the two terminals of the terminal portion is also secured.

With the above-described structure, the leakage and entering of the reference electrode internal solution to a portion above the reference electrode chamber is prevented, so that the insulation between the glass electrode internal electrode and the reference electrode internal electrode is secured. As a result, it is possible to provide a combination electrode for ion concentration measurement capable of stably measuring ion concentration.

EXAMPLES

Hereinafter, the present invention will be described in further detail based on examples by referring to the drawings. However, the present invention is not limited to these examples.

Example 1

Figure 1:
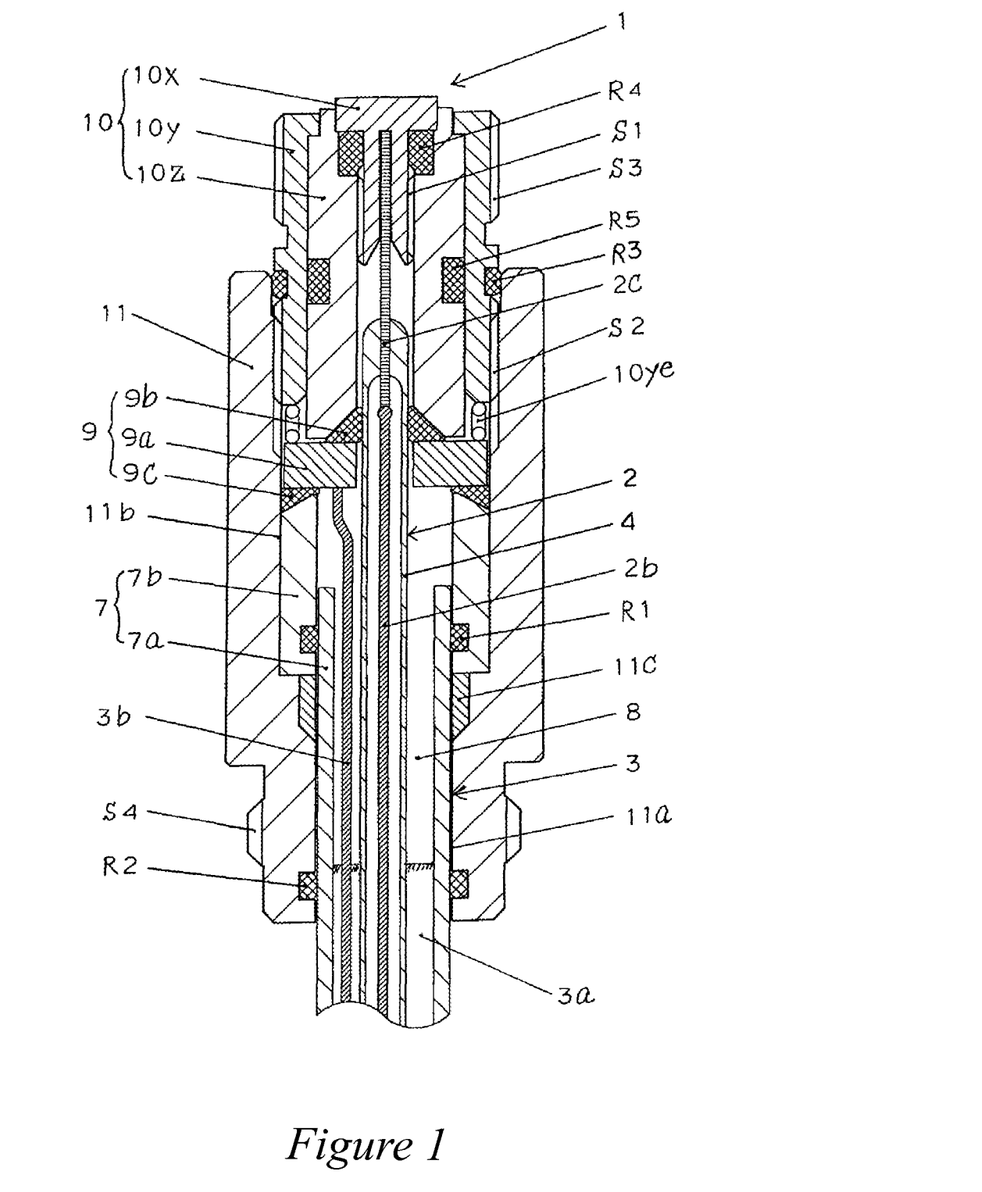
FIG. 1 is an enlarged partial schematic cross-sectional view showing an example of a main portion of a combination electrode for ion concentration measurement of the present invention.

FIG. 1 is an enlarged partial schematic cross-sectional view showing an example of a main portion of a combination electrode for ion concentration measurement of the present invention, i.e., a portion centering at a sealing portion of a reference electrode chamber.

In this figure, a combination electrode 1 for ion concentration measurement of the present invention includes a glass electrode 2 and a reference electrode 3.

Note that structures of lower portions (including a sensitive glass membrane, a liquid junction, and the like) of the glass electrode 2 and the reference electrode 3 are not shown in the figure. The structures are substantially the same as those of the glass electrode 52 and the reference electrode 53 of the conventional combination electrode 51 for ion concentration measurement shown in FIG. 4.

Specifically, the glass electrode 2 has a glass support tube 4 (Example of its outer diameter: 2.5 mm) whose upper end is sealed by melting, and which has a sensitive glass membrane (not illustrated) at its lower end.

Here, an electric potential generated on a surface of the sensitive glass membrane is taken out of the glass support tube 4, generally through a glass electrode internal solution (not illustrated) housed inside the sensitive glass membrane and a platinum wire 2c which is connected to an end portion of a silver wire of silver-silver chloride serving as a glass electrode internal electrode 2b, in the glass support tube 4, and which penetrates an upper end-sealing portion. Then, the electric potential is transmitted to a lead wire (not illustrated) to a potentiometer through a terminal 10x for a glass electrode.

The reference electrode 3 has a closed reference electrode chamber 8 whose upper and lower surfaces are sealed, and a reference electrode internal electrode 3b made of silver-silver chloride and a reference electrode internal solution 3a (a potassium chloride solution or the like) housed in the reference electrode chamber 8. Here, the reference electrode chamber 8 is formed inside an outer tube 7 having a liquid junction (not illustrated) near a lower end thereof, and around the glass support tube 4 placed penetrating the outer tube 7 along a substantially center axis thereof, (the outer tube 7 including a glass outer tube 7a (Example of its outer diameter: 6 mm) and an outer tube extension 7b (a joint tube (a collar) made of PPS (Polyphenylene-sulfide) having insulating properties, Example of its diameters: its outer diameter: 9 mm and its inner diameter: 6.2 mm) which is an upward extension into which an upper portion of the glass outer tube 7a is liquid-tightly fitted with an O-ring or the like R1 interposed in between).

Note that the reference electrode internal solution 3a contains 3% (W/V) of a thickener (Example: the above-described CMC).

In an insulating connecting member 11 (Example of its material: the above-described PPS) for connecting the outer tube 7 and a terminal portion 10 thereabove to each other, an insertion hole 11a having a small diameter (the diameter being substantially equal to the outer diameter of the glass outer tube 7a) is formed in a lower portion of the connecting member 11, and a fitting hole 11b having a large diameter (the diameter being substantially equal to the outer diameter of the outer tube extension 7b) is formed upwardly from an upper end of the insertion hole 11a. By inserting the glass outer tube 7a through the insertion hole 11a from above, the outer tube extension 7b is also fitted into the fitting hole 11b. The outer tube 7 is mounted on and fixed to the connecting member 11 by positioning a lower end of the outer tube extension 7b at a lower end of the fitting hole 11b.

Note that reference sign R2 denotes an O-ring or the like for securing liquid tightness. In addition, to fix the connecting member 11 and the outer tube 7 to each other more securely, the two may be fixed to each other with bond by: providing an adhesive agent space 11c on an inner surface of the insertion hole 11a.

In addition, all of the O-rings or the like R1 and R2, and other O-rings or the like R3 to 5, which will be described later, are shown in distorted states.

An upper surface of the reference electrode chamber 8 is sealed at a position of an upper end of the outer tube extension 7b by a sealing means 9 of the present invention, which will be described later in detail. Meanwhile, a lower surface (not illustrated) of the reference electrode chamber 8 is sealed by being melt and integrally welded to a lower end of a glass support tube 4, for example.

The terminal portion 10 placed above the outer tube 7 includes: a cylindrical insulating member 10z having a large thickness; the terminal 10x for a glass electrode, and a terminal 10y for a reference electrode. The terminal 10x has a T-shape, and is screed to an upper portion of the insulating member 10z by means of a screw portion S1. The terminal 10y has a cylindrical shape, and is fitted onto an outer periphery of the insulating member 10z.

Note that an inward flange formed at an upper end of the terminal 10y is fitted onto a notch portion formed in an outer periphery of the upper end of the insulating member 10z.

Then, the terminal portion 10 and the connecting member 11 are screwed to each other by means of a screw portion S2 between a lower outer periphery of the terminal 10y and an upper inner periphery of the connecting member 11, and are liquid-tightly connected to each other with the O-ring or the like R3 interposed in between.

Note that the platinum wire 2c led out of an upper end-sealing portion of the glass support tube 4 inserted into the insulating member 10z from below is connected to the terminal 10x. Reference signs R4, R5 denote O-rings or the like for securing liquid tightness.

The sealing means 9 on an upper surface of the reference electrode chamber 8 includes: an annular silver member 9a (having a disk shape with an inner diameter slightly larger than the outer diameter of the glass support tube 4 and an outer diameter slightly smaller than the diameter of the fitting hole 11b of the connecting member 11 (substantially equal to the outer diameter of the outer tube extension 7b), Example of its thickness: 2 mm) which the glass support tube penetrates along a center axis thereof; an annular sealing elastic member 9b (an inner elastic member, Example: an O-ring of an ethylene-propylene-diene rubber (EPDM)) which is located on an upper surface of the silver member 9a, and which liquid-tightly seals a space between an inner periphery of the silver member 9a and an outer periphery of the glass support tube 4; and an annular elastic member 9c (an outer elastic member, Example: the above-described O-ring of EPDM) which is located on a lower surface of the silver member 9a, and which liquid-tightly seals a space between the silver member 9a and the outer tube extension 7b.

In addition, an end portion of the silver wire of the reference electrode internal electrode 3b is connected to the lower surface of the silver member 9a in advance by welding or the like.

Moreover, the upper surface of the silver member 9a is connected to a lower end of the terminal 10y with a conductive member 10ye (Example: a stainless steel spring) or the like, which is expandable and contractible in the vertical direction, interposed in between.

A taper whose diameter becomes gradually larger toward a lower end is formed in a lower end surface of the insulating member 10z slightly projecting beyond the lower end of the terminal 10y, and a taper whose diameter becomes gradually larger toward a upper end is formed in an upper end surface of the outer tube extension 7b. The elastic member 9b is housed in a mounting portion surrounded by the former taper, the upper surface of the silver member 9a, and the outer periphery of the glass support tube 4. Meanwhile, the elastic member 9c is housed in a mounting portion surrounded by the latter taper, the lower surface of the silver member 9a, and an inner surface of the fitting hole 11b of the connecting member 11 (corresponding to the above-described auxiliary tube).

When the upper surface of the reference electrode chamber 8 is sealed by the sealing means 9, the terminal portion 10 is screwed downwardly into the connecting member 11 by means of the screw portion S2. Thereby, the insulating member 10z (functioning as an external-force application member) is lowered, and an appropriate external force is applied to the elastic member 9b, and further to the elastic member 9c through the elastic member 9b and the silver member 9a. As a result, the elastic members 9b, 9c are pressed against the inside of the mounting portions, and take distorted state as shown in the figure.

In this way, the space between the inner periphery of the silver member 9a and the outer periphery of the glass support tube 4, and the space between the silver member 9a and the outer tube extension 7b (the outer tube in the present invention) are liquid-tightly sealed.

In addition, an electric potential of the reference electrode internal electrode 3b is transmitted to a lead wire (not illustrated) to a potentiometer through the terminal 10y.

Note that a screw portion S3 is provided on the upper outer periphery of the terminal 10y, and enables a connecting portion of the lead wire to be screwed thereon.

In addition, prior to the sealing of the upper surface of the reference electrode chamber 8, a portion near an upper end surface in the glass outer tube 7a (here, the portion near the upper end surface in the glass outer tube 7a refers to an intermediate portion of the reference electrode chamber 8 above the surface of the reference electrode internal solution 3a) may be sealed by a filler of a synthetic resin (Example: a silicone resin).

Moreover, a screw portion S4 for the mounting to a culture apparatus may be provided in a lower portion of the connecting member 11.

As described above, in the combination electrode 1 for ion concentration measurement of the present invention, the leakage and entering of the reference electrode internal solution 3a to a portion above the reference electrode chamber 8 due to thermal cycles of a conventional sterilization treatment is prevented, so that insulation is secured between the glass electrode internal electrode 2b and the reference electrode internal electrode 3b. Hence, the combination electrode 1 for ion concentration measurement is capable of stably measuring ion concentration.

Example 2

Figure 2:
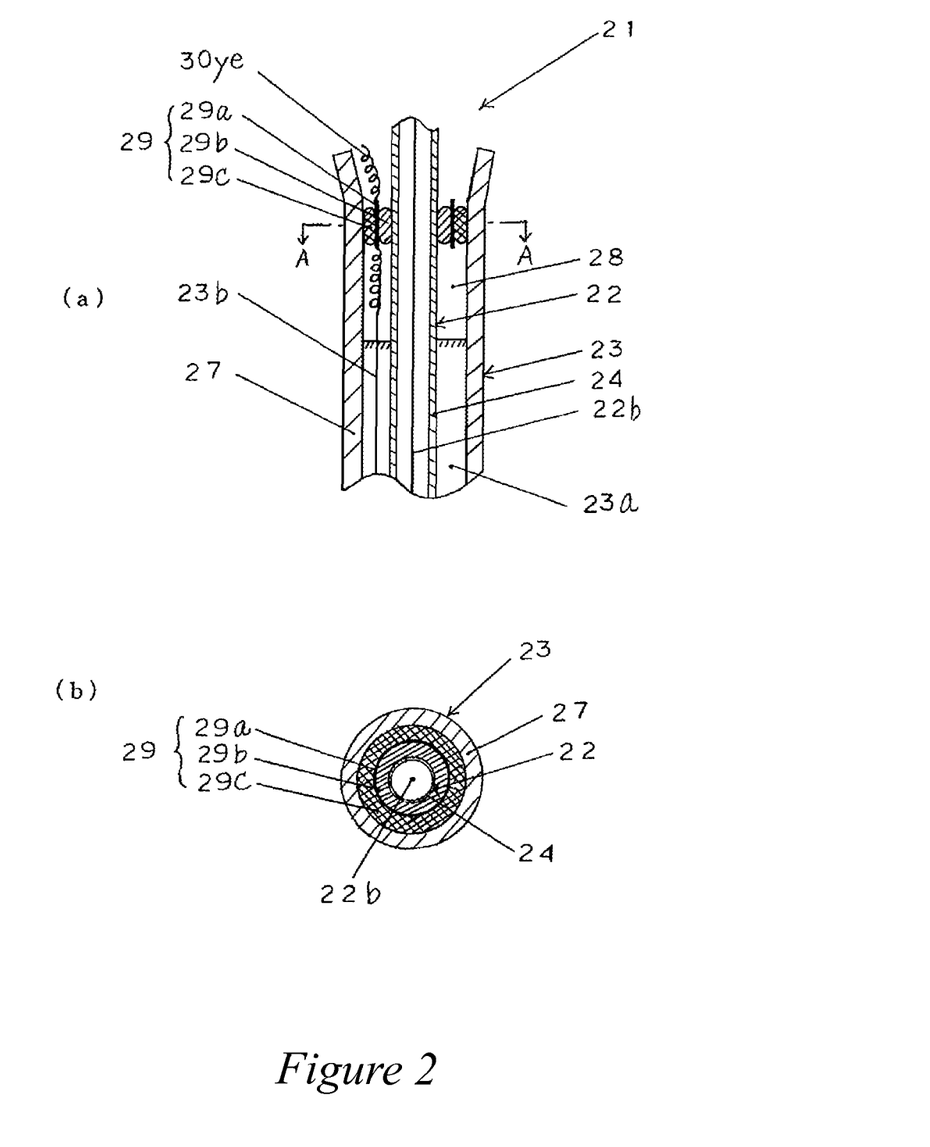
FIG. 2 is enlarged partial schematic cross-sectional views showing another example of the main portion of the combination electrode for ion concentration measurement of the present invention.

FIG. 2 is enlarged partial schematic cross-sectional views showing another example of the main portion of the combination electrode for ion concentration measurement of the present invention, i.e., an example where the sealing portion of the reference electrode chamber is in the outer tube and near the upper end thereof. Here, Part (b) is a cross-sectional view of the main portion taken along the line A-A of Part (a).

Note that the structures of the lower portions of a glass electrode 22 and a reference electrode 23, excluding the structures of their other portions near the sealing portion of an upper surface of a reference electrode chamber 28, as well as the structures of a connecting member, a terminal portion and the like are substantially the same as those described in Example 1, and are not shown in the figure.

The upper surface of the reference electrode chamber 28 is sealed at a position in an outer tube 27 and near the upper end thereof.

In a sealing means 29 used in this case, an annular elastic member 29b (an inner elastic member, Example: an O-ring similar to that described in Example 1) is fitted into an inner periphery of an annular silver member 29a (having a cylindrical shape, Example: its thickness: 0.5 mm, its height: 4 mm, its inner diameter: sufficiently larger than the outer diameter of the glass support tube 24, its outer diameter: sufficiently smaller than the inner diameter of the outer tube 27) which a glass support tube 24 penetrates along a substantially center axis thereof. In addition, another annular elastic member 29c (an outer elastic member, Example: an O-ring similar to that described in Example 1) is fitted onto an outer periphery of the annular silver member 29a. Here, the inner diameter of the inner elastic member (29b) is smaller than the outer diameter of the glass support tube 24, and the outer diameter of the inner elastic member (29b) is larger than the inner diameter of the annular silver member 29a. In addition, the outer diameter of the outer elastic member (29c) is larger than the inner diameter of the outer tube 27, and the inner diameter of the outer elastic member (29c) is smaller than the outer diameter of the annular silver member 29a.

Note that an end portion of a silver wire of a reference electrode internal electrode 23b has a spiral shape expandable and contractible in the vertical direction, and is connected to a lower end of a silver member 29a by welding in advance. Meanwhile, an upper end of the silver member 29a is connected to a terminal (not illustrated) for a reference electrode through a conductive member 30ye expandable and contractible in the vertical direction, for example, after the mounting of the sealing means 29.

For mounting the sealing means 29 into the outer tube 27, a method is employed in which the sealing means 29 is gradually inserted into the outer tube 27 by applying an external force to the sealing means 29 through an upper end opening of the outer tube 27, which is formed in advance in a funnel shape whose diameter becomes gradually larger toward an upper end thereof, by use of an appropriate external-force application accessory member capable of uniformly pressing the upper surface of the sealing means 29, with the glass support tube 24 being inserted into the sealing means 29 from a portion below the elastic member 29b, for example.

Thereby, the elastic members 29b, 29c are distorted as shown in the figure, and liquid-tightly seal a space between the inner periphery of the silver member 29a and the outer periphery of the glass support tube 24, and a space between the outer periphery of the silver member 29a and the inner periphery of the outer tube 27.

Note that the height of the cylinder-shaped silver member 29a is preferably a height with which the upper end and the lower end of the silver member 29a are exposed in a state (mounted state) where the elastic members 29b, 29c are distorted in the outer tube 27, from the viewpoint that the silver wire of the reference electrode internal electrode 23b and the conductive member 30ye are connected to the silver member 29a.

In addition, reference sign 23a denotes a reference electrode internal solution.

As described above, the connecting member (not illustrated) for connecting the outer tube 27 and the terminal portion (not illustrated) thereabove is substantially the same as that described in Example 1. However, since the portion near the upper end of the outer tube 27 is shaped like a funnel in this embodiment, this portion may be located at a lower end of a fitting opening of the connecting member.

Note that, prior to the sealing of the upper surface of the reference electrode chamber 28, a portion below a position at which the sealing means 29 is provided may also be sealed by a filler (Example: a silicone resin). In this case, the filler also functions as a supporting member for supporting the sealing means 29 from below.

A combination electrode 21 for ion concentration measurement in which the upper surface of the reference electrode chamber 28 is thus sealed can achieve the same effect as can that described in Example 1.

Example 3

Figure 3:
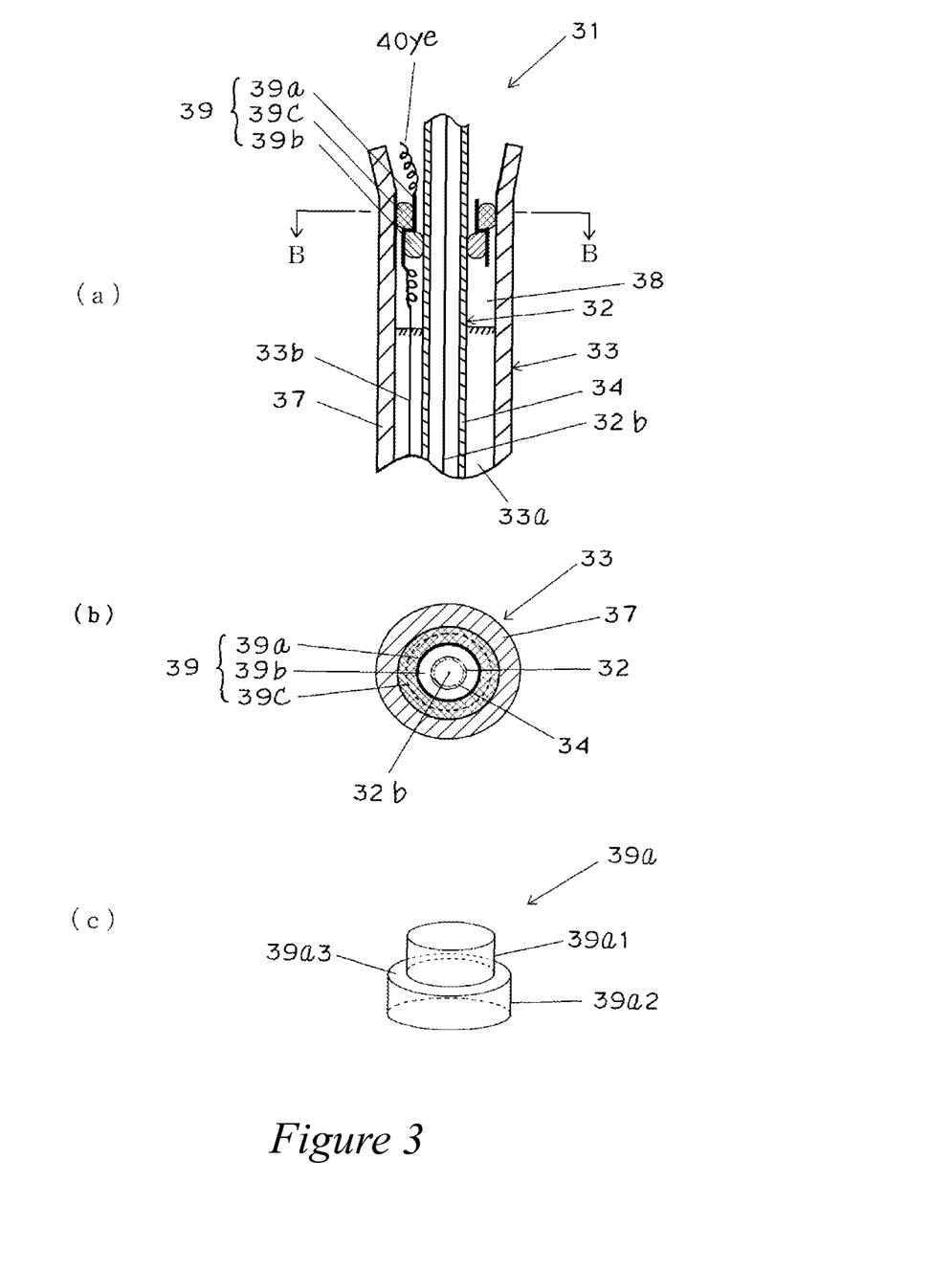
FIG. 3 is enlarged partial schematic cross-sectional views showing a still another example of the main portion of the combination electrode for ion concentration measurement of the present invention.

FIG. 3 is enlarged schematic partial cross-sectional view and the like showing still another example of the main portion of the combination electrode for ion concentration measurement of the present invention, i.e., an embodiment where the sealing portion of the reference electrode chamber is in the outer tube and near the upper end thereof. Here, Part (a) is a cross-sectional view of the main portion, Part (b) is a cross-sectional view of the main portion taken along the line B-B of Part (a), and Part (c) is a perspective view of an annular silver member shown in Parts (a) and (b).

In this figure, the main portion of the combination electrode for ion concentration measurement has substantially the same structure as that described in Example 2, except that the annular silver member has an integrated two-staged cylindrical shape.

Specifically, an upper surface of a reference electrode chamber 38 is sealed at a position in an outer tube 37 and near an upper end thereof.

As shown in FIG. 3(c), an annular silver member 39a in a sealing means 39 used in this case is an integrated two-staged cylinder (a kind of cylindrical shape) in which an upper end portion of a cylinder 39a2 having a large diameter is connected to a lower end portion of a cylinder 39a1 having a small diameter through a doughnut-shaped circular plate 39a3. Here, the inner diameter of the cylinder 39a1 at the upper stage is sufficiently larger than the outer diameter of a glass support tube 34, and the outer diameter of the cylinder 39a2 at the lower stage is sufficiently smaller than the inner diameter of an outer tube (Example: their thickness: 0.5 mm, the height of each cylinder: 4 mm).

In addition, in the sealing means 39, an annular elastic member 39b (an inner elastic member, Example: an O-ring similar to that described in Example 2) is fitted into an inner periphery of the cylinder 39a2 at the lower stage of the annular silver member 39a (a kind of cylindrical shape) which a glass support tube 34 penetrates along a substantially center axis thereof. Moreover, another annular elastic member 39c (an outer elastic member, Example: an O-ring similar to that described in Example 2) is fitted onto an outer periphery of the cylinder 39a1 at the upper stage. Here, the inner diameter of the inner elastic member (39b) is smaller than the outer diameter of the glass support tube 34, and the outer diameter of the inner elastic member (39b) is larger than the inner diameter of the cylinder 30a2 at the lower stage. Meanwhile, the outer diameter of the outer elastic member (39c) is larger than the inner diameter of the outer tube 37, and the inner diameter of the outer elastic member (39c) is smaller than the outer diameter of the cylinder 39a1 at the upper stage.

Note that an end portion of a silver wire of a reference electrode internal electrode 33b has a spiral shape expandable and contractible in the vertical direction, and is connected, to a lower end of the silver member 39a by welding in advance. Meanwhile, an upper end of the silver member 39a is connected to a terminal (not illustrated) for a reference electrode through a conductive member 40ye expandable and contractible in the vertical direction after the mounting of the sealing means 39, for example.

For mounting the sealing means 39 into the outer tube 37, a method is employed in which, as in the case with Example 2, the sealing means 39 is gradually inserted into the outer tube 37 by applying an external force to the sealing means 39 through an upper end opening of the outer tube 37, which is formed in advance in a funnel shape whose diameter becomes gradually larger toward an upper end thereof, by use of an appropriate external-force application accessory member capable of uniformly pressing the upper surface of the sealing means 39, with the glass support tube 34 being inserted into the sealing means 39 from a portion below the elastic member 39b, for example.

Thereby, the elastic members 39b, 39c are distorted as shown in the figure, and liquid-tightly seal the space between the inner periphery of the silver member 39a and the outer periphery of the glass support tube 34, and the space between the outer periphery of the silver member 39a and the inner periphery of the outer tube 37.

Note that reference sign 33a denotes a reference electrode internal solution.

Alternatively, the sealing means 39 inverted in the vertical direction can also be used as the sealing means, of course.

A combination electrode 31 for ion concentration measurement in which the upper surface of the reference electrode chamber 38 is thus sealed can achieve the same effects as can that described in Example 1.

REFERENCE SIGNS LIST 1, 21, 31, 51 combination electrode for ion concentration measurement
2, 22, 32, 52 glass electrode
2b, 22b, 32b, 52b glass electrode internal electrode
2c, 52c platinum wire
3, 23, 33, 53 reference electrode
3a, 23a, 33a, 53a reference electrode internal solution
3b, 23b, 33b, 53b reference electrode internal electrode
4, 24, 34, 54 glass support tube
7, 27, 37, 57 outer tube
7a glass outer tube
7b outer tube extension
8, 28, 38, 58 reference electrode chamber
9, 29, 39, 59 sealing means
9a, 29a, 39a annular silver member
9b, 29b, 39b annular elastic member
9c, 29c, 39c annular elastic member
10, 60 terminal portion
10x, 60x terminal for glass electrode
10y, 60y terminal for reference electrode
10z, 60z insulating member
11, 61 connecting member
11a insertion hole
11b fitting hole
52a glass electrode internal solution
55 sensitive glass membrane
56 liquid junction
62 space portion and the like

The invention claimed is:

1. A combination electrode for ion concentration measurement, comprising a glass electrode and a reference electrode, wherein the glass electrode includes a glass support tube, and a sensitive glass membrane at a lower end of the glass support tube, the reference electrode includes a closed reference electrode chamber whose upper and lower surfaces are sealed, a reference electrode internal electrode made of silver-silver chloride, and a reference electrode internal solution, the reference electrode chamber being formed inside an outer tube having a liquid junction near a lower end thereof and around the support tube placed penetrating the outer tube along a substantially center axis thereof, the reference electrode internal electrode and the reference electrode internal solution being housed in the reference electrode chamber, a sealing means configured to seal the upper surface of the reference electrode chamber includes: an annular silver member which the glass support tube penetrates along a substantially center axis thereof; and annular sealing elastic members for liquid-tightly sealing a space between an inner periphery of the silver member and an outer periphery of the glass support tube, and a space between the silver member and the outer tube, respectively, wherein the annular sealing elastic members are each distorted and in direct contact with the annular silver member, such that the space between the inner periphery of the annular silver member and the outer periphery of the glass support tube and the space between the annular silver member and the outer tube are liquid-tightly sealed, and the reference electrode internal electrode is connected to a terminal for a reference electrode through the silver member.

2. The combination electrode for ion concentration measurement according to claim 1, wherein the annular silver member has any one of a disk shape and a cylindrical shape.

3. The combination electrode for ion concentration measurement according to claim 1, wherein the annular sealing elastic members are made of rubber.

4. The combination electrode for ion concentration measurement according to claim 2, wherein the annular sealing elastic members are made of rubber.

* * * * *